United States Patent [19]

Nickl et al.

[11] Patent Number: 4,753,934
[45] Date of Patent: Jun. 28, 1988

[54] ACRYLIC ACID HETEROCYCLIC AMIDES, FUNGICIDAL COMPOSITIONS AND USE

[75] Inventors: Josef Nickl; Helmut Pieper, both of Biberach an der Riss; Jürgen Curtze, Geisenheim-Johannisberg; Christo Drandarevski, Ingelheim; Sigmund Lust, Darmstadt, all of Fed. Rep. of Germany

[73] Assignee: Celamerck GmbH & Co. KG, Ingelheim am Rhein, Fed. Rep. of Germany

[21] Appl. No.: 913,136

[22] Filed: Sep. 29, 1986

Related U.S. Application Data

[63] Continuation of Ser. No. 583,770, Feb. 27, 1984, abandoned.

[30] Foreign Application Priority Data

Feb. 28, 1983 [DE] Fed. Rep. of Germany ....... 3306996
Mar. 7, 1983 [DE] Fed. Rep. of Germany ....... 3308045

[51] Int. Cl.⁴ .................... A01N 43/40; A01N 43/84; C07D 295/18

[52] U.S. Cl. ................ 514/231.5; 514/318; 514/326; 514/330; 514/378; 514/422; 514/423; 514/233.8; 514/235.5; 514/237.5; 514/237.2; 514/231.8; 514/232.2; 514/232.5; 544/58.2; 544/58.4; 544/82; 544/85; 544/79; 544/86; 544/87; 544/130; 544/137; 544/148; 544/158; 544/159; 544/163; 544/165; 544/172; 544/173; 544/174; 544/176; 546/187; 546/189; 546/196; 546/209; 546/226; 548/240; 548/524; 548/526; 548/540; 564/74; 564/161; 564/162; 564/163; 564/166; 564/167; 564/168; 564/171; 564/174

[58] Field of Search ........ 544/58.2, 58.4, 79, 544/82, 85, 86, 87, 130, 137, 148, 158, 159, 163, 165, 172, 173, 174, 176; 546/187, 189, 196, 209, 226; 548/240, 524, 526, 540; 514/222, 228, 232, 233, 234, 236, 237, 238, 240, 318, 326, 330, 378, 422, 423

[56] References Cited

PUBLICATIONS

Eicher et al., Chemical Abstracts, vol. 81 (1974) No. 91085t.

Primary Examiner—Robert W. Ramsuer
Attorney, Agent, or Firm—Weissenberger, Hammond & Littell

[57] ABSTRACT

Compounds of the formula

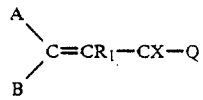

wherein A, B, $R_1$, X and Q are substituents of various types, and acid addition salts thereof. The compounds are useful as fungicides.

8 Claims, No Drawings

ACRYLIC ACID HETEROCYCLIC AMIDES, FUNGICIDAL COMPOSITIONS AND USE

This is a continuation of Ser. No. 583,770, filed Feb. 27, 1984, now abandoned.

This invention relates to novel acrylic acid amides and acid addition salts thereof, to methods of preparing these compounds, to fungicidal compositions containing them as active ingredients, and to a method of using them as agricultural fungicides.

More particularly, the present invention relates to a novel class of acrylic acid amides represented by the formula

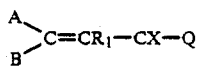    (I)

wherein
A is

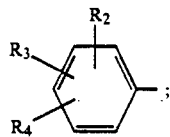    (II)

B is
$Y-(CR_5=CR_6)_k$;    (III)

Q is

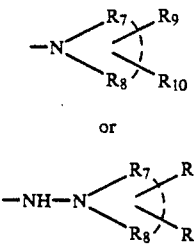    (IV)

or (V)

X is =O, =S or =NH;

Y is $C_{3-10}$ alkyl or, when k is 1 or 2, also $C_{1-2}$ alkyl; or substituted $C_{1-10}$ alkyl; or an optionally substituted radical selected from the group consisting of $C_{3-7}$ alkenyl, $C_{3-7}$ cycloalkyl, $C_{5-7}$ cycloalkenyl, pyridyl, furyl, thienyl, α- and β-naphthyl; or together with $-CR_5=$ is a 5- to 7-membered, preferably saturated, cycloaliphatic group onto which a benzene ring may be condensed; or

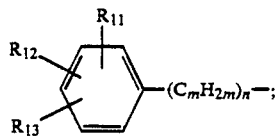    (VI)

k is 0, 1 or 2;
m is 1, 2, 3 or 4;
n is 0 or 1;
$R_1$ is hydrogen, $C_{1-4}$ alkyl, cyano and, when k is 0, also chlorine, bromine or iodine;
$R_2$ and $R_{11}$ are each hydrogen, halogen, nitro, $C_{1-4}$ alkyl, alkoxy optionally mono- or polysubstituted by fluorine or chlorine, $C_{3-4}$ alkynyloxy, amino, $-NH(C_{1-4}$ alkyl), $-N(C_{1-4}$ alkyl)$_2$, cyano, phenyl, $C_{3-6}$ cycloalkyl, $C_{3-4}$ alkenyloxy, hydroxy($C_{1-4}$ alkyl), $-NH-COR_6$, $-CO_2R_6$, $-CONR_7R_8$, $C_{2-8}$ alkyl interrupted by oxygen, or

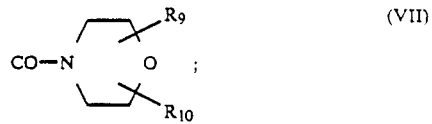    (VII)

$R_3$, $R_4$, $R_{12}$ and $R_{13}$ are each hydrogen, halogen, $C_{1-4}$ alkyl, $C_{1-4}$ alkoxy, $(C_{1-4}$ alkyl)-$S(O)_p$ (p=0, 1 or 2), hydroxy or $(C_{1-4}$ alkanoyl)oxy; or $R_3/R_4$ and $R_{12}/R_{13}$ together are methylene dioxy or ethylenedioxy attached to two adjacent carbon atoms of the phenyl ring;

$R_5$ and $R_6$ are each hydrogen or $C_{1-4}$ alkyl;

$R_5$ may also, together with the C atom to which it is attached and Y, be a 5- to 7-membered, preferably saturated, cycloaliphatic group onto which a benzene ring may be condensed;

$R_7$ and $R_8$ are each $C_{1-4}$ alkyl, $C_{3-7}$ cycloalkyl, phenyl, benzyl, furfuryl, tetrahydrofuryl or $C_{3-4}$ alkenyl, or together are a $C_{3-5}$ alkylene chain which may be interrupted by $-O-$, $-NR_6-$ or $-S(O)_q-$ where q=0, 1 or 2); or $R_7$ may be hydrogen; and $R_9$ and $R_{10}$, which are only present when $R_7$ and $R_8$ together are an alkylene chain, are each hydrogen or $C_{1-4}$ alkyl;

with the proviso that A and B are other than both phenyl, monohalophenyl, mononitrophenyl or monoaminophenyl, and non-toxic, pharmacologically acceptable acid addition salts thereof.

Within the scope of the above definitions, the radicals and groups may be identical or different.

The substituents in the groups given for Y are, in particular, halogen, nitro, amino, $C_{1-4}$ alkyl and alkoxy groups optionally mono- or polysubstituted by halogen, $-NH(C_{1-4}$ alkyl), $-N(C_{1-4}$ alkyl)$_2$, phenoxy, phenylthio or $C_{1-4}$ alkylthio.

The carbon chains of the alkyl, alkoxy, alkyl—$S(O)_p$, mono- or dialkylamino groups preferably contain 1-3, more particularly 1 or 2 carbon atoms. If the chains have more than 2 carbon atoms they may be either unbranched or branched. "Halogen" means fluorine, chlorine, bromine or iodine, particularly chlorine or bromine.

The group A is preferably di- or tri-substituted, while two substituents, for instance methyl, methoxy, ethyl, ethoxy, fluorine, chlorine, bromine, $-CF_3$, $-CF_2Cl$, $CF_3O-$, $CH_3S-$, $CH_3SO-$, $CH_3SO_2-$, $-NH_2$, $-NHCH_3$, $-N(CH_3)_2$, $-O-CH_2-O-$ or $-O-C_2H_4-O-$, are preferably in the 3,4-position.

Q preferably represents a group of the formula IV wherein $R_7$ and $R_8$ together represents an optionally interrupted alkylene chain, so that IV represents, for example, groups of the following type:

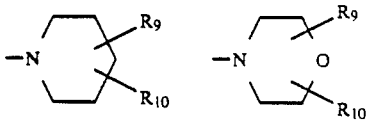

-continued

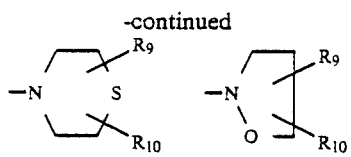

If A and B in formula I are different, the compounds of the formula I may be present as cis-trans isomers. In this case, formula I comprises both the individual isomers and also mixtures of the cis- and trans-compound.

The compounds embraced by formula I may be prepared by the following methods which involve known chemical synthesis principles:

Method A

Reaction of an acrylic acid of the formula

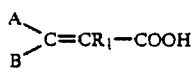  (VIII)

wherein A, B and $R_1$ have the meanings previously defined, or a reactive derivative thereof, optionally prepared in situ, with a compound of the formula

H—Q  (IX)

wherein Q has the meanings previously defined, or with an N-activated derivative of compound IX, optionally prepared in situ (in which case the acid VIII itself is used).

The process is thus the acylation of a compound of the formula IX with a carboxylic acid of the formula VIII in the presence of an acid-activating or dehydrating agent or with reactive derivatives of the acid, or reaction of a carboxylic acid of the formula VIII with a compound of the formula IX in the presence of an agent which activates the amino group or with reactive derivatives of the amine. End products are obtained wherein X represents oxygen.

Examples of reactive derivatives of a carboxylic acid of the formula VIII, optionally prepared in the reaction mixture, include the alkyl, aryl, aralkyl esters of thioesters thereof, such as methyl, ethyl, phenyl or benzyl esters; the imidazolides; acid halides such as the acid chloride or bromide, the anhydrides; the mixed anhydrides with aliphatic or aromatic carboxylic, sulfenic, sulfinic, sulfonic acids, or with carbonic acid esters, such as acetic acid, propionic acid, p-toluenesulfonic acid or O-ethylcarbonic acid; or the N-hydroxyimide esters thereof. Suitable reactive derivatives of an amine of formula IX, optionally prepared in the reaction mixture, include for example the "phosphorusazo derivatives".

The nature of the hydrocarbon radicals in the above-mentioned groups is not particularly critical. Alkyl groups generally contain between 1 and 12 carbon atoms, may be straight or branched and may be interrupted by oxygen or sulfur. Aryl groups preferably contain 6 or 10 carbon atoms, aralkyl groups 7 to 12 carbon atoms, while the alkyl moiety may contain 1 to 6 carbon atoms, and the aromatic moiety may also be substituted by $C_{1-3}$ alkyl (in which case the aryl-substituted alkyl group would correspondingly comprise fewer carbon atoms). The aromatic rings may also optionally have a mixture of substituents, such as one or more $C_{1-2}$ alkyl groups, $C_{1-2}$ alkoxy and/or one or more halogen atoms.

Examples of acid-activating and/or dehydrating agents include chloroformates such as ethylchloroformate, phosphorus pentoxide, N.N'-dicyclohexylcarbodiimide, N.N'-carbonyldiimidazole or N,N'-thionyldiimidazole.

The reaction is advantageously carried out in a solvent or mixture of solvents, such as methylene chloride, chloroform, carbon tetrachloride, ethyl, tetrahydrofuran, dioxane, benzene, toluene, acetonitrile or dimethylformamide, optionally in the presence of an inorganic base such as sodium carbonate or a tertiary organic base such as triethylamine or pyridine, which may simultaneously act as the solvent, and optionally in the presence of an acid-activating agent at temperatures of between $-25°$ C. and $150°$ C., but preferably at temperatures of between $-10°$ C. and the boiling point of the reaction mixture. There is no need to isolate any reactive derivative of a compound of the general formula VIII or IX which may be formed in the reaction mixture, and furthermore the reaction may also be carried out in an excess of the compound of the formula IX as the solvent.

Method B

Reaction of a ketone of the formula

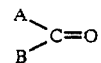  (X)

wherein A and B have the meanings previously defined, with a phosphonic acid derivative of the formula

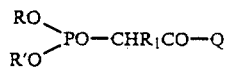  (XI)

wherein $R_1$ and Q have the meanings previously defined, and R and R', which may be identical to or different from each other, are each straight or branched $C_{1-12}$ alkyl groups, $C_{7-12}$ aralkyl groups or $C_{6-10}$ aryl groups. The alkyl chains may be interrupted by oxygen or sulfur, and the aryl and aralkyl group may be mono- or polysubstituted by halogen, $C_{1-2}$ alkyl or alkoxy at the nucleus. R and R' preferably represent $C_{1-3}$ alkyl groups.

The reaction is carried out in the presence of a basic substance such as sodium hydride, potassium tert.butoxide, sodium methoxide or sodium amide, preferably in a solvent which is sufficiently inert under the reaction conditions, such as tetrahydrofuran, dioxane, 1,2-dimethoxyethane, dimethylformamide, benzene, toluene or mixtures of such solvents, at temperatures between $0°$ and $150°$ C., preferably between $0°$ C. and the boiling point of the reaction mixture. An excess of the compound of the formula XI may also be used as the reaction medium.

Method C

To prepare a compound of the formula I wherein X represents sulfur (thioamides), the corresponding amide is reacted with phosphorus pentasulfide in an inert solvent.

Suitable solvents include, for example, toluene, xylene or benzene. The reaction temperature is between $0°$ C. and the boiling point of the reaction mixture, although generally a temperature of 120° C. need not be exceeded.

Method D

To prepare a compound of the formula I wherein X represents =NH (amidines), a corresponding imino-ester of the formula

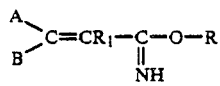 (XII)

wherein A, B, R and $R_1$ have the meanings previously defined, is reacted with an amine of the formula IX.

The reaction is carried out in an inert solvent such as ether or tetrahydrofuran, at temperatures between about 0° and 100° C.

Method E

In order to prepare a compound of the formula I, wherein k represents 0 (in group III) and $R_1$ represents halogen, particularly chlorine or bromine, the halogen is added to the double compound of the acrylic acid grouping in a corresponding starting compound, and hydrogen halide is subsequently split off at elevated temperatures.

The reaction is carried out in inert solvents such as glacial acetic acid, or preferably with the addition of glacial acetic acid, at temperatures between about 30° and 100° C.

Method F

To prepare a compound of the formula I wherein $R_1$ represents —CN, a corresponding compound wherein $R_1$ represents halogen is reacted with copper(I)cyanide in an inert solvent.

Suitable inert solvents include, for example, dimethylformamide and dimethylsulfoxide. The reaction temperature is preferably between 70° and 180° C.

Method G

In order to prepare a compound of the formula I wherein $R_1$ represents cyano, a ketone of the formula X may also be reacted with a cyanoacetic acid derivative of the formula

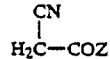 (XIII)

wherein Z represents the group Q or the group OR, where Q and R have the meanings previously defined.

The reaction is carried out in an inert solvent such as benzene or toluene, preferably using a water separator, and in the presence of a catalyst such as ammonium acetate/glacial acetic acid, at elevated temperatures, preferably at the boiling point of the reaction mixture. If Z in compound XIII represents the group —OR, this is replaced by the group Q according to method A.

Method H

To prepare a compound of the formula I wherein the groups A and/or B contain optionally acylated phenolic hydroxy groups, a corresponding compound of the formula I wherein the groups A and/or B contain lower to medium ($C_{1-12}$) alkoxy groups or benzyloxy groups in the corresponding position is subjected to ether splitting and is optionally subsequently acylated.

The ether splitting is carried out with conventional agents, for example with hydrogen bromide/glacial acetic acid at elevated temperatures. A reactive derivative of the acid to be introduced, for instance the acid chloride or acid anhydride, may be used for the acylation.

Method I

To prepare a compound of the formula I wherein A and/or B contain amino groups, a corresponding nitro compound is reduced by conventional methods.

The reducing agent may be, for example, sodium dithionite, while the reaction medium may be an inert solvent, such as ethanol/water. The reaction temperature is between room temperature and about 100° C.

Mixtures of cis and trans isomers obtained according to the invention may, if desired, subsequently be separated by conventional methods into the individual cis and trans isomers.

Separation of the isomers is preferably carried out by fractional crystallization, for instance by crystallization from methanol, ethanol, isopropanol, methanol/water or ethanol/petroleum ether.

Those compounds of the formula I which contain basic groups form additional salts with inorganic or organic acids. Examples of non-toxic, pharmacologically acceptable acid addition salts are those formed with hydrochloric, hydrobromic, sulfuric or phosphoric acid or the like.

The starting materials are known or may be prepared by conventional methods analogous to known compounds, while compounds of the formula VIII wherein B represents the group III and k is 1 or 2 may, for example, be obtained by the following reaction sequence:

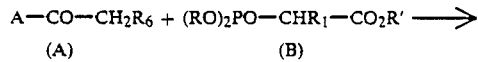

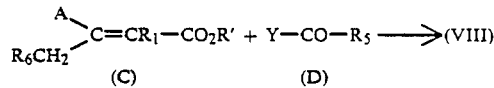

where A, R, R', $R_1$, $R_5$, $R_6$ and Y have the meanings previously defined. R preferably represented a lower alkyl group such as methyl or ethyl. R' is preferably a $C_{1-3}$ alkyl group. The olefination step of B to C may, for example be carried out by using the Horner variant of Wittig's Reaction.

Ketones of the formula X may be obtained, for example, by Friedel-Crafts acylation of a corresponding benzene with 4-nitrobenzoyl chloride, reduction of the nitro group and subsequent halogenation, or by reacting aniline hydrochloride with methylal in the presence of acetic anhydride, oxidation with chromium trioxide, splitting off of the acetyl groups and subsequent halogenation.

Starting materials of the formuls VIII wherein A and B are phenyl groups may be obtained by reacting a corresponding benzophenone of the formula X with a phosphonoacetic acid compound of the formula

 (XIV)

wherein R, R' and $R_1$ have the meanings previously defined and R" represents a lower alkyl group, in the presence of a base, followed by hydrolysis of the ester group.

Compounds of the formula

wherein A, B, $R_1$ and R have the meanings previously defined, which are required as starting materials may also be obtained by the Reformatsky method

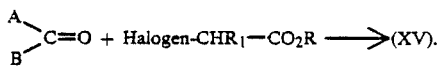

Starting materials of the type

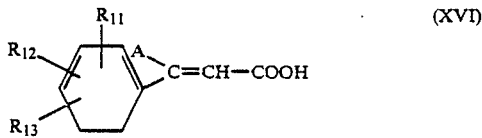

wherein A, $R_{11}$, $R_{12}$ and $R_{13}$ have the meanings previously defined, may be obtained by the reaction

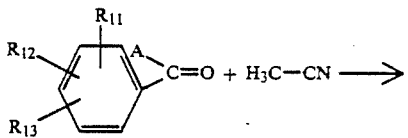

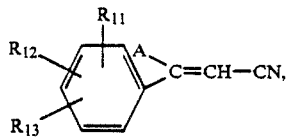

followed by hydrolysis.

The following examples illustrate the present invention and will enable others skilled in the art to understand it more completely. It should be understood, however, that the invention is not limited solely to the particular examples given below.

PREPARATION OF STARTING COMPOUNDS

Example A

4'-Chloro-4-nitro-benzophenone

A mixture of 100 g (0.54 mol) of 4-nitro-benzylchloride, 100 g (0.75 mol) of aluminum chloride and 100 ml (111 g; 0.99 mol) of chlorobenzene was heated at 80° C., while stirring, under exclusion of moisture from air, to form a melt. After the evolution of hydrogen chloride had ended, the temperature was increased to 100° C. and the mixture was stirred for another half hour at this temperature. After being cooled to about 40°–50° C., the viscous liquid reaction mixture was poured onto ice, whereupon a white precipitate was formed which was suction-filtered off and washed with ethanol.

Melting point: 100°–102° C.

Example B

4-Amino-4'-chloro-benzophenone

A hot solution of 13 g (0.05 mol) of 4'-chloro-4-nitrobenzophenone in 80 ml of ethanol was added in small portions, while stirring, to a hot solution of 53.5 g (0.24 mol) of tin(II)chloride dihydrate in 50 ml of concentrated hydrochloric acid, which was accompanied by a violent reaction. After all had been added, the mixture was heated on a steam bath for two hours and was then poured into an aqueous potassium hydroxide solution, while stirring. A precipitate was formed which was suction-filtered off and dissolved in boiling ethanol. The insoluble matter was filtered off, and the filtrate was allowed to cool. The light yellow crystals which precipitated were suction-filtered off.

Melting point: 184°–185° C.

Example C

4-Amino-3,4',5-trichloro-benzophenone 23.2 g (0.1 mol) of 4-amino-4'-chloro-benzophenone were dissolved in 200 ml of tetrahydrofuran. 400 ml of glacial acetic acid were added to this solution, and then a solution of 14.2 g (0.2 mol) of chlorine in 150 ml of glacial acetic acid was quickly added thereto, while vigorously stirring and cooling with ice. The mixture was stirred for 5 minutes more, and was then poured into water. A white precipitate was obtained which was suction-filtered off and crystallized from ethanol.

Melting point: 165°–167° C.

Example D 4,4'-diacetoamino-diphenylmethane 76 g (1 mol) of methylal were added dropwise, while stirring, to a solution of 260 g (2 mol) of aniline hydrochloride in 600 ml of water. After all had been added, the mixture was heated at 60° C. for one hour and then at 90° C. for 3 hours, while the methanol which formed was distilled off. After cooling, the solution was combined with a concentrated solution of 40 g of sodium hydroxide, while being cooled with ice. An oil was precipitated which crystallized upon further stirring. The crystals were suction-filtered off and taken up in 2 liters of a mixture of chloroform and 10N sodium hydroxide solution. The chloroform solution was separated, dried over sodium sulfate and evaporated to dryness in vacuo. The residue was dissolved in 1 liter of benzene, and the solution was mixed with petroleum ether until oily impurities separated out. After decantin, the remaining benzene-petroleum ether solution was poured into about 1 liter of petroleum ether, while vigorously stirring, whereupon 4,4'-diamino-diphenylmethane precipitated as an oil. This fractional precipitation was repeated twice. The oily 4,4'-diamino-diphenylmethane thus obtained was dissolved in the least possible amount of glacial acetic acid, 205 g (2 mol) of acetic anhydride were added dropwise thereto, while stirring, and the resulting mixture was then heated at 120° C. for one hour. After cooling, the mixture was poured into about 3 liters of water, and the precipitated crystals were suction-filtered off and washed with water.

Melting point: 228°–230° C.

Example E

4,4'-Diamino-benzophenone 100 g of chromic acid anhydride were dissolved in 50 ml of water, and the solution was brought up to 240 ml with glacial acetic acid. 97 ml of this solution were slowly added to a solution of 77 g of 4,4'-diacetamino-diphenylmethane, while stirring and cooling, while care was taken to ensure that the temperature did not rise above 40° C. Then the mixture was heated at 90° C. for one hour, while further stirring, then cooled and poured into ice water. An oily product was precipitated which crystallized after being allowed to stand for some time. The precipitated crystals were suction-filtered off, washed with water and then heated for 5 minutes at reflux temperature in 92 ml of 66% sulfuric acid. After cooling, the solution was poured into water, and the aqueous solution was made alkaline with 10N sodium hydroxide, whereupon crude 4,4'-diamino-benzophenone precipitated.

Melting point: 247°-248° C. (ethanol).

Example F

4,4'-Diamino-3,3',5,5'-tetrachloro-benzophenone 25 g (0.12 mol) of 4,4'-diamino-benzophenone were dissolved in a mixture of 25 ml of concentrated hydrochloric acid, 200 ml of water and 500 ml of glacial acetic acid. While vigorously stirring and cooling with ice water, the solution was rapidly combined with a solution of 33.5 g (0.42 mol) of chlorine in 400 ml of glacial acetic acid, stirred for two minutes more and poured over ice. The precipitate was suction-filtered off and crystallized from ethanol/water.

Melting point: 237°-239° C.

PREPARATION OF END PRODUCTS OF THE FORMULA I

The isomer whose >C=CH-CO-proton appeared at a low field intensity in the NMR-spectrum was designated isomer A in the following examples.

Example 1

(a) Ethyl 4-amino-β-(4-chlorophenyl)-3,5-dichloro-cinnamate

A solution of 108 g (0.55 mol) of ethyl diethylphosphonoacetate in 150 ml of dry 1,2-dimethoxyethane was slowly added dropwise, while stirring and cooling with ice to a suspension of 13.2 g (0.55 mol) of sodium hydride (26.4 g of 50% oil suspension) in 50 ml of dry 1,2-dimethoxyethane, whereupon the mixture foamed vigorously. After all the solution had been added the mixture was stirred for another 30 minutes. It was then combined with a suspension of 150 g (0.5 mol) of 4-amino-3,4',5-trichloro-benzophenone in 800 ml of dry 1,2-dimethoxyethane and heated for one hour at reflux temperature, whereby a clear solution was formed. The solution was evaporated to dryness in vacuo, and the residue was distributed between chloroform and water. The organic phase was dried and evaporated to dryness in vacuo. After mixing with 150 ml of ethanol, crystallization set in. The crystals were suction-filtered off and washed with ethanol and petroleum ether.

Melting point of the mixture of isomers A and B: 88°-110° C.

NMR-spectrum (CDCl₃, 60 MHz):

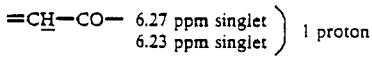

1 proton

After two recrystallizations from ethanol/petroleum ether, crystals of the pure isomer A were obtained, melting point 124°-125° C.

NMR-spectrum (CDCl₃, 60 MHz): —C$\underline{H}$—CO— 6.27 ppm singlet (1 proton)

(b) 4-Amino-β-(4'-chlorophenyl)-3,5-dichloro-cinnamic acid 136 g (0.368 mol) of ethyl 4-amino-β-(4'-chlorophenyl)-3,5-dichloro-cinnamate (mixture of isomers A and B) were refluxed for one hour in a mixture of 1000 ml of ethanol and 300 ml of 5N sodium hydroxide. After cooling, the mixture was diluted with water and acidified with 2N hydrochloric acid. An initially oily product was precipitated which crystallized after a short time. The crystals were suction-filtered off and recrystallized from ethanol. Colorless crystals of the pure isomer A were obtained, melting point 241°-243° C. (decomp.).

NMR-spectrum (DMSO, 60 MHZ): =C$\underline{H}$—CO 6.37 ppm singlet (1 proton)

By further evaporation of the mother liquor another crystal fraction was obtained, melting point 200°-204° C. (decomp.), which consisted of a mixture of isomers A/B-1/1.5.

NMR-spectrum (DMSO, 60 MHz):

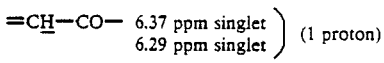

(1 proton)

(c) 4-Amino-β-(4-chlorophenyl)-3,5-dichloro-cinnamic acid morpholide 20 g (0.058 mol) of 4-amino-β-(4-chlorophenyl)-3,5-dichloro-cinnamic acid (mixture of isomers A and B in the ratio 1:1.5) were dissolved in 700 ml of dry chloroform. 5.93 g (0.058 mol) of triethylamine were added while cooling with ice and stirring, and the mixture was cooled to −10° C. and combined with 6.35 g (0.058 mol) of ethyl chloroformate. After the addition had ended, 25.5 g (0.29 mol) of morpholine were added while further stirring and cooling. The resulting mixture was stirred for 4 hours more at room temperature and then extracted three times with water, and the organic phase was dried over sodium sulfate and concentrated to dryness in vacuo. The residue was chromatographed on a silica gel column (silica gel: substance=10:1, eluant: chloroform/ethyl acetate=1:1). The eluates containing substance were combined and evaporated to dryness in vacuo. Colorless crystals were obtained, melting point 140°-144° C., which contained the cis/trans isomer mixture in a proportion of 3:2.

NMR-spectrum (CDCl₃, 80 MHz):

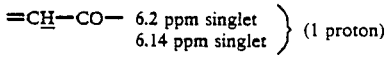

(1 proton)

By recrystallizing the cis/trans isomer mixture from ethanol, the pure trans isomer was obtained, melting point 168°-171° C.

NMR-spectrum (CDCl$_3$, 80 MHz): —C$\underline{H}$—CO— 6.2 ppm singlet (1 proton).

The steric condition of the compound of formula

[Chemical structure diagram showing a compound with 4-amino-3,5-dichlorophenyl group and 4'-chlorophenyl group attached to C=C, with C-N morpholide group, labeled with H$_A$, H$_A'$, H$_B'$, H$_C$]

thus prepared was elucidated by $^1$H-NMR-spectroscopy at 90 MHz. This showed the signals
(a) H$_A$ of the 4-amino-3,5-dichloro-phenyl ring at 7.09 ppm (singlet).
(b) H$_A'$ and H$_B'$ of the 4-chlorophenyl ring at 7.23 ppm (doublet) and at 7.33 ppm (doublet).
(c) H$_C$ of the olefin at 6.22 ppm (singlet).

The olefinic H of the isomeric compound (isomer B) was observed at 6.17 ppm, as was established by the spectrum of the isomer mixture.

NOE measurements was carried out in order to clarify the steric situation of the olefinic double bond. (The Nuclear Overhauser Effect, J. H. Noggle, R. E. Schirmer, Academic Press New York and London 1971). The NOE measurements were carried out using a 90 MHz FT-NMR apparatus (Bruker Model HX-90/15") on a 2% solution of the substance in specially dried and degassed CDCl$_3$.

The NOE measurement, homonuclear in the $^1$H-NMR spectrum at 90 MHz, gave the following results:

| Signal of H atom radiated | Signal of H atom observed | Change in intensity % |
|---|---|---|
| Hc (6.22 ppm) | H$_A$ (7.09 ppm) | +14 to 15 |
| Hc (6.22 ppm) | H$_A'$ (7.23 ppm) | +3 to 5 |
| Hc (6.22 ppm) | H$_B'$ (7.33 ppm) | +1 to 3 |

The intensity measurements (Table) show that the spatial gap between Hc and H$_A$ is substantially smaller than between Hc and H$_A'$. The compound of the above formula was thus present in the trans form illustrated.

Example 2

4-Amino-β-(4'-chlorophenyl)-3,5-dichloro-cinnamic acid morpholide

A solution of 5.3 g (0.02 mol) of diethylphosphonoacetic acid morpholide in 100 ml of dry tetrahydrofuran was slowly added dropwise, while stirring, to a suspension of 1 g of sodium hydride (0.02 mol, 50% in oil) in 50 ml of dry tetrahydrofuran. Slight heating and strong foaming occurred. After all had been added, the mixture was stirred for 10 minutes more. A solution of 3 g (0.01 mol) of 4-amino-3,4',5-trichlorobenzophenone in 20 ml of dry tetrahydrofuran was added dropwise to the resulting clear solution, and the mixture was heated for 16 hours at reflux temperature. After cooling, the solution was poured into water, and the aqueous mixture was extracted exhaustively with methylene chloride. The methylene chloride phase was dried with sodium sulfate and evaporated by evaporation in vacuo. The residue was crystallized from isopropanol/petroleum ether. The colorless crystals thus obtained, melting point 150°–155° C., contained the cis/trans isomers in a ratio of 1:3.

NMR-spectrum (CDCl$_3$, 80 MHz):

=C$\underline{H}$—CO— 6.2 ppm singlet  
6.14 ppm singlet  } (1 proton)

By recrystallizing the cis/trans isomer mixture from ethanol, the pure trans isomer was obtained, melting point 168°–171° C.

NMR-cpectrum (CDCl$_3$, 80 MHz): =C$\underline{H}$—CO— 6.2 ppm singlet (1 proton)

Example 3

4-Amino-β-(4'-chloro-phenyl)-3,5-dichloro-cinnamic acid morpholide

This compound was prepared from 4-amino-3,4',5-trichlorobenzophenone, diethylphosphonoacetic acid morpholide and potassium tert.butoxide in dimethylformamide analogous to Example 4.

Purification by column chromatography and crystallization from isopropanol/petroleum ether.

Melting point of the cis/trans isomer mixture in the ratio 1:3; 150°–155° C.

NMR-spectrum (CDCl$_3$, 80 MHz):

=C$\underline{H}$—CO— 6.2 ppm singlet  
6.14 ppm singlet  } (1 proton)

Example 4 trans-4-Amino-β-(4'-chlorophenyl)-3,5-dichloro-cinnamic acid morpholide

This compound was prepared from the 4-amino-β-(4'-chlorophenyl)-3,5-dichloro-cinnamic acid isomer A with ethyl chloroformate and morpholine analogous to Example 3.

Melting point: 168°–171° C.

NMR-spectrum (CDCl$_3$, 80 MHz): =CH—CO— 6.2 ppm singlet (1 proton).

Example 5

4-Amino-β-(4'-amino-3',5'-dichlorophenyl)-3,5-dichloro-cinnamic acid morpholide 16.2 g (0.061 mol) of diethylphosphonoacetic acid morpholide were dissolved in 100 ml of dry tetrahydrofuran, and 1.5 g (0.061 mol) of sodium hydride (2.7 g of a 55% oil suspension) were added in small portions thereto. After all had been added, the mixture was stirred for 30 minutes and was then combined with a solution of 18 g (0.051 mol) of 4,4'-diamino-3,3'-5,5'-tetrachlorobenzophenone, and the resulting mixture was refluxed for 18 hours. After cooling, the solution was poured into ice water, and the aqueous mixture was exhaustively extracted with a total of 2 liters of methylene chloride. The methylene chloride phase was dried over sodium sulfate and evaporated in vacuo. The residue was suspended in 200 ml of methylene chloride, and the suspension was briefly boiled. After cooling, the crystalline product was suction-filtered.

Melting point: 256°–258° C.

Example 6

4-Amino-β-(4-bromophenyl)-3,5-dibromo-cinnamic acid morpholide

This compound was prepared from 4-amino-β-(4'-bromophenyl)-3,5-dibromo-cinnamic acid (isomer ratio A:B=1.5:1), ethyl chloroformate, triethylamine and morpholine analogous to Example 3.

Melting point of the 2.5:1 mixture of isomers A and B: 165°–180° C.

NMR-spectrum (CDCl$_3$, 80 MHz):

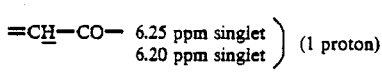

Example 7

4-Amino-β-(4'-chlorophenyl)-3,5-dibromo-cinnamic acid morpholide

This compound was prepared from 4-amino-β-(4'-chlorophenyl)-3,5-dibromo-cinnamic acid (isomer ratio A:B=5:1), ethyl chloroformate, triethylamine and morpholine analogous to Example 1(c).

Melting point of the 6:1 mixture of isomers A and B: 178°–189° C.

NMR-spectrum (CDCl$_3$, 80 MHz):

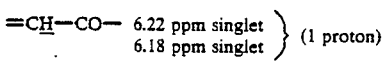

Example 8

4-Amino-3,5-dibromo-β-(4'-fluorophenyl)-cinnamic acid morpholide

This compound was prepared from 4-amino-3,5-dibromo-β-(4'-fluorophenyl)-cinnamic acid (isomer ratio A:B=2.5:1), ethyl chloroformate, triethylamine and morpholine analogous to Example 1(c).

Melting point of the 4:1 mixture of isomers A and B: 186°–197° C.

NMR-spectrum (CDCl$_3$, 80 MHz):

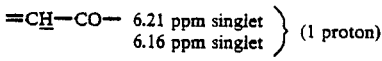

Example 9

4-Amino-3,5-dibromo-β-phenyl-cinnamic acid morpholide

This compound was prepared from 4-amino-3,5-dibromo-β-phenyl-cinnamic acid (isomer ratio A:B=1:1), ethyl chloroformate, triethylamine and morpholine analogous to Example 1(c). Melting point of the 1:1 mixture of isomers A and B: 156°–174° C.

NMR-spectrum (CDCl$_3$, 400 MHz):

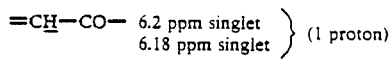

Example 10

4-Amino-β-(4'-bromophenyl)-3,5-dichloro-cinnamic acid morpholide

This compound was prepared from 4-amino-β-(4'-bromophenyl)-3,5-dichloro-cinnamic acid (isomer ratio A:B=1:2.5), ethyl chloroformate, triethylamine and morpholine analogous to Example 1(c).

Melting point of the pure isomer A: 188°–194° C.

NMR-spectrum (CDCl$_3$, 60 MHz) =C$\underline{H}$—CO— 6.23 ppm singlet (1 proton).

Example 11

4-Amino-3,5-dichloro-β-(4'-fluorophenyl)-cinnamic acid morpholide

This compound was prepared from 4-amino-3,5-dichloro-β-(4'-fluorophenyl)-cinnamic acid (isomer ratio A:B=3:1), ethyl chloroformate, triethylamine and morpholine analogous to Example 1(c).

Melting point of the 3:1 mixture of isomers A and B: 160°–176° C.

NMR-spectrum (CDCl$_3$, 60 MHz):

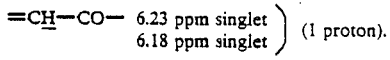

Example 12

4-Amino-3,5-dichloro-β-phenyl-cinnamic acid morpholide

This compound was prepared from 4-amino-3,5-dichloro-β-phenyl-cinnamic acid (isomer ratio A:B=1.5:1), ethyl chloroformate, triethylamine and morpholine analogous to Example 1(c).

Melting point of the 1:1 mixture of isomers A and B: 143°–160° C.

NMR-spectrum (CDCl$_3$, 400 MHz):

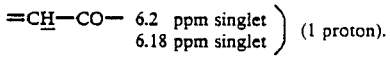

Example 13

(a) 3-Bromo-4-dimethylaminobenzophenone

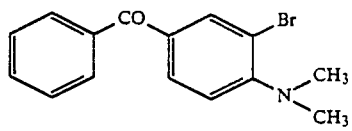

22.5 g (0.1 mol) of 4-dimethylaminobenzophenone were dissolved in 60 ml of acetic acid, and then a solution of 5.3 ml (0.105 mol) of bromine in 20 ml of acetic acid was added dropwise thereto over a period of one hour, while stirring. The mixture was then stirred for 30 minutes more, and some water and some sodium bisulfite for decolorization were added. The greasy substance thus obtained was shaken with toluene/water, the toluene phase was washed twice more with water and dried, and the toluene was distilled off in vacuo. Yield: 24.4 g (80% of theory); viscous oil.

(b) 3-Bromo-4-dimethylamino-β-phenyl cinnamic acid

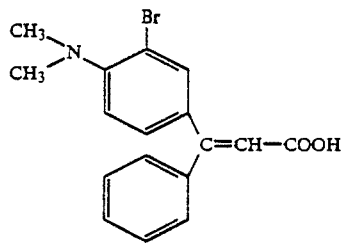

2.1 g (0.07 mol) of sodium hydride (containing 20% paraffin oil) were stirred with 30 ml of absolute 1,2-dimethoxyethane, and, while cooling with ice water, a solution of 15.7 g (0.07 mol) of triethylphosphono-acetate in 30 ml of 1,2-dimethoxyethane was added dropwise thereto. When a clear solution was formed, a solution of 18.25 g (0.06 mol) of 3-bromo-4-dimethylaminobenzophenone in 30 ml of 1,2-dimethoxyethane was added. The mixture was refluxed for 4 hours and, after standing overnight, the solvent was distilled off in vacuo. The residue was shaken with toluene/water, the toluene phase was washed again with water and dried, and the toluene was distilled off in vacuo. The residue was hydrolized by refluxing for 2 hours with a methanolic potassium hydroxide solution consisting of 14 g (0.25 mol) of potassium hydroxide and 250 ml of methanol +25 ml of water. The solution was concentrated in vacuo, and the residue was shaken with toluene/water.

The aqueous solution was adjusted to pH 6.5 by the addition of hydrochloric acid, whereupon the product precipitated in solid form. The product was soluble in excess hydrochloric acid. After washing with water it was dried.

Yield: 15.2 g (73% of theory);
Melting point: 147° C.

(c) 3-Bromo-4-dimethylamino-β-phenyl-cinnamic acid morpholide

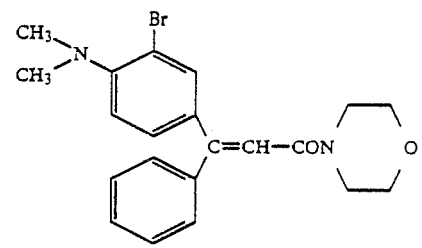

5.19 g (15 mmols) of 3-bromo-4-dimethylamino-β-phenylcinnamic acid were dissolved in 30 ml of absolute tetrahydrofuran, and 3.24 g (20 mmols) of 1,1'-carbonyldiimidazole are added in small portions to the solution. After the evolution of $CO_2$ had ended and a clear solution was formed, 1.74 g (20 mmols) of morpholine were added, and the mixture was allowed to stand for 10 minutes at room temperature and was then refluxed for 30 minutes. The resulting solution was evaporated in vacuo, and the residue was shaken with toluene/water. The toluene phase was washed twice more with water, dried and evaporated in vacuo. The oil thus obtained crystallized on being triturated with a little methanol.

Yield: 6.25 g (91.5% of theory);
M.p. 169° C.
Rf: 0.55 (toluene/acetone 70:30).

Using the procedure analogous to those described in the preceding examples, the compound of the formula

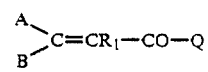

shown in the following table were also prepared:

TABLE I

| Example | A | B | Q | $R_1$ | M.p. (°C.) | Rf |
|---------|---|---|---|-------|------------|-----|
| 14 | ![Br, OCH3 phenyl] | $C_6H_5$ | —N(morpholine)O | H | oil | 0.51* |
| 15 | ![Cl, N(CH3)2 phenyl] | $C_6H_5$ | —N(morpholine)O | H | | |
| 16 | ![Cl, OH, Cl phenyl] | $C_6H_5$ | —N(morpholine)O | H | 174 | |

TABLE I-continued

| Example | A | B | Q | $R_1$ | M.p. (°C.) | Rf |
|---|---|---|---|---|---|---|
| 17 | 2-NH₂, 3,6-dichlorophenyl | C₆H₅ | morpholino | H | 136 | |
| 18 | 2-NH₂, 3-Br, 6-Cl-phenyl | C₆H₅ | morpholino | H | 75–80 | |
| 19 | 2,3-dichlorophenyl | 4-Cl-phenyl | morpholino | H | oil | |
| 20 | 2,3-dimethoxyphenyl | 4-OCH₃-phenyl | morpholino | H | | |
| 21 | 2-Br, 3-OCH₃-phenyl | 2-Br, 3-OCH₃-phenyl | morpholino | H | 93 | |
| 22 | 2-Cl, 3-N(CH₃)₂-phenyl | 2-Br, 3-N(CH₃)₂-phenyl | morpholino | H | oil | 0.55* |
| 23 | 2-Cl, 3-OCH₃, 6-Cl-phenyl | C₆H₅ | morpholino | H | oil | 0.57* |
| 24 | 2-Br, 3-OCH₃-phenyl | C₆H₅ | 2,6-dimethylmorpholino | H | oil | 0.49 & 0.59* |
| 25 | 2,6-dichloro-3-NH₂-phenyl | 4-Cl-phenyl | 2,6-dimethylmorpholino | H | oil | 0.58* |

TABLE I-continued

| Example | A | B | Q | $R_1$ | M.p. (°C.) | Rf |
|---|---|---|---|---|---|---|
| 26 | 4-CH₃, 2-NO₂-phenyl | C₆H₅ | 3,5-dimethylmorpholino | H | | |
| 27 | 4-(isobutyl)phenyl (CH₂CH(CH₃)CH₃) | C₆H₅ | morpholino | H | | |
| 28 | 3-Cl, 4-[N(n-C₄H₉)(CH₃)]-phenyl | 4-Br-phenyl | morpholino | H | | |
| 29 | 2-CH₃, 4-Br-phenyl | 2-CH₃, 4-Br-phenyl | 3-(n-C₄H₉)morpholino | H | | |
| 30 | 2-NO₂, 4-Cl-phenyl | 2-NO₂, 4-Cl-phenyl | 3-ethylmorpholino | H | | |
| 31 | 2,5-Cl₂, 4-Br-phenyl | 2,5-Cl₂, 4-Br-phenyl | morpholino | CH₃ | | |
| 32 | 3-Cl, 4-OCH₃-phenyl | 3-Cl, 4-OCH₃-phenyl | 5-methylmorpholino | n-C₄H₉ | | |
| 33 | C₆H₅ | 4-N(CH₃)₂-phenyl | morpholino | H | 142 | |
| 34 | 2,5-(CH₃)₂-phenyl | C₆H₅ | morpholino | H | 120 | |
| 35 | 2,4-(CH₃)₂-phenyl | C₆H₅ | morpholino | H | | 0.55* |

TABLE I-continued

| Example | A | B | Q | R₁ | M.p. (°C.) | Rf |
|---|---|---|---|---|---|---|
| 36 | 2-Cl, 4-NO₂ phenyl | C₆H₅ | —N(morpholino) | H | | |
| 37 | 3,4-di-OCH₃ phenyl (with additional OCH₃) | 2,3-di-OCH₃ phenyl | —N(morpholino) | H | | 0.34* |

*Rf values: eluant toluene/acetone 7:3. Polygram TLC plates made by the Macherey-Nagel Co. (Serial No. 805 021) were used; 22° C.

Example 38

3-(3,4-Dimethoxyphenyl)-5-phenylpenta-2,4-diene-1-carboxylic acid morpholide (a) Ethyl 3,4-dimethoxy-β-methyl-cinnamate

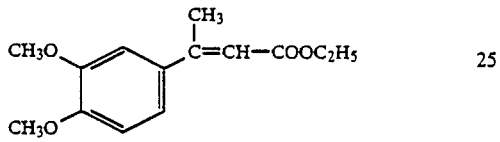

24.75 g (825 mmols) of sodium hydride (containing 20% of paraffin oil) were stirred with 300 ml of absolute 1,2-dimethoxyethane, and 185 g (825 mmols) of triethylphosphonoacetate were added dropwise thereto, while cooling with ice water. 135 g (750 mmols) of 3,4-dimethoxy-acetophenone were added to the clear solution all at once, and the resulting mixture was refluxed for 3 hours, while stirring, on a boiling water bath. After standing overnight, the 1,2-dimethoxyethane was distilled off in vacuo, and the residue was extracted with toluene/water. The toluene solution was again washed with water and dried, and the foluene was distilled off in vacuo. The residue was fractionally distilled in vacuo.

Yield: 159 g (85% of theory).
B.p. 130° C./0.04 mbar.

(b) 3-(3,4-Dimethoxyphenyl)-5-phenylpenta-2,4-diene-1-carboxylic acid

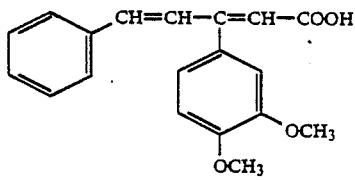

5.05 g (45 mmols) of potassium tert. butoxide were dissolved in 20 ml of absolute dimethylformamide, and a solution of 10.0 g (40 mmols) of ethyl 3,4-dimethoxy-β-methylcinnamate and 4.78 g (45 mmols) of benzaldehyde in 10 ml of absolute dimethylformamide was added dropwise thereto, while stirring and cooling on an ice bath. The mixture was then stirred for 4 hours at room temperature, combined with water and acidified with hydrochloric acid. The greasy substance obtained thereby was stirred with hot water, and sodium carbonate was added in batches until a solution was obtained. This aqueous solution was extracted twice with toluene. Upon acidification with hydrochloric acid, the product was precipitated, and after washing with water it was recrystallized from toluene.

Yield: 9.7 g (78% of theory).
M.p. 164° C.

(c) 3-(3,4-Dimethoxyphenyl)-5-phenylpenta-2,4-diene-1-carboxylic acid morpholide

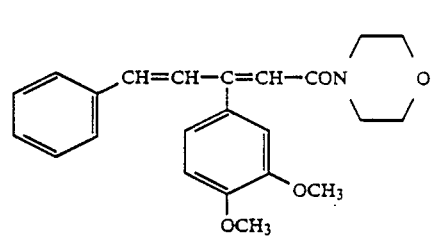

4.66 g (15 mmols) of 3-(3,4-dimethoxyphenyl)-5-phenyl-penta-2,4-diene-1-carboxylic acid were dissolved in 30 ml of absolute tetrahydrofuran, and 3.24 g (20 mmols) of 1,1'-carbonyldiimidazole were added to the solution in batches. After evolution of $CO_2$ had ended and a clear solution was obtained, 1.74 g (20 mmols) of morpholine were added, and the mixture was allowed to stand for 10 minutes at room temperature and was then refluxed for 30 minutes. The resulting solution was evaporated in vacuo, and the residue was shaken with toluene/water. The toluene solution was washed twice more with water, dried and evaporated in vacuo.

Yield: 4.9 g (86% of theory); pure oil according to TLC.

Rf: 0.54 (toluene/acetone 70:30)

Analysis: Calc.: C-72.80%, found: 73.12%; Calc.: H-6.64%, found: 6.67%; Calc.: N- 3.69%, found: 3.64%.

Example 39

(a)

5-(4-Chlorophenyl)-3-(3,4-dimethoxyphenyl)-hexa-2,4-diene-1-carboxylic acid

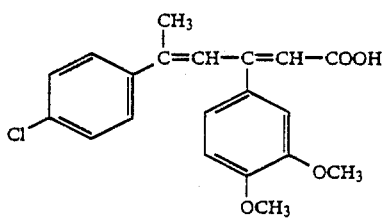

5.05 g (45 mmols) of potassium tert. butoxide were dissolved in 20 ml of absolute dimethylformamide, and a solution of 10.0 g (40 mmols) of ethyl 3,4-dimethoxy-β-methylcinnamate and 6.96 g (45 mmols) of 4-chloroacetophenone in 10 ml of absolute dimethylformamide was added dropwise thereto, with stirring and cooling on an ice bath. The mixture was then stirred for 4 hours at room temperature, mixed with water and acidified with hydrochloric acid. The viscous oil thus obtained was stirred with hot water, and sodium carbonate was added in portions until a solution was formed. The aqueous solution was washed once with toluene. Upon acidification with hydrochloric acid, the product was again obtained in the form of an oil. The oil was extracted with toluene, the extract was washed twice with water and dried, and the toluene was distilled off in vacuo.

Yield: 11.9 g (83% of theory; oil).

(b)

5-(4-Chlorophenyl)-3-(3,4-dimethoxyphenyl)-hexane-2,4-diene-1-carboxylic acid morpholide

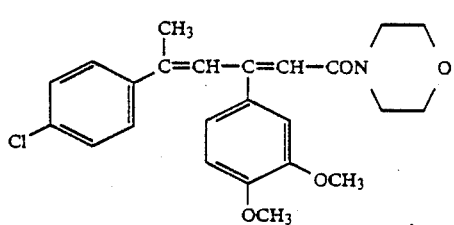

5.38 g (15 mmols) of 5-(4-chlorophenyl)-3,4-dimethoxyphenyl)-hexa-2,4-diene-1-carboxylic acid were dissolved in 30 ml of absolute tetrahydrofuran, and 3.24 g (20 mmols) of 1,1'-carbonyldiimidazole were added in portions thereto. After the evolution of CO₂ had ended, 1.74 g (20 mmols) of morpholine were added, the mixture was allowed to stand at room temperature for 10 minutes and was then refluxed for 30 minutes. The resulting solution was evaporated in vacuo, and the residue was shaken with toluene/water. The toluene phase was again washed with water, dried and concentrated to about 20 ml in vacuo. This solution was purified on a chromatography column charged with 30 g of silica gel mixed with toluene. Elution is carried out first with toluene, then with a toluene/acetone mixture (90:10). The fractions containing the substance with an Rf 0.47 (toluene/acetone 70:30 on silica gel plate) are collected and evaporated in vacuo.

Yield: 4.7 g (73% theory), oil

Analysis: C calc. 67.36%, found 67.38%, H calc. 6.12%, found 6.22%, N calc. 3.27%, found 3.13%.

Example 40

(a) Ethyl 3-(3,4-dimethoxyphenyl)-2-methylcrotonate

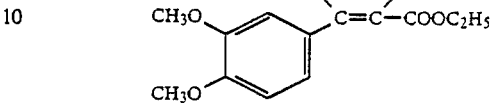

3.3 g (110 mmols) of sodium hydride (containing 20% paraffin oil) were stirred with 40 ml of absolute 1,2-dimethoxyethane, and 26.2 g (110 mmols) of triethyl-2-phosphonopropionate were added dropwise thereto, while cooling with ice water. After a clear solution had been obtained, 18 g (100 mmols) of 3,4-dimethoxyacetophenone were added, and the mixture was refluxed for 3 hours while stirring. After standing overnight, the 1,2-dimethoxyethane was distilled off in vacuo, and the residue was shaken with toluene/water. The toluene phase was again washed with water and dried, and the toluene was distilled off in vacuo. The residue was fractionally distilled in vacuo.

Yield: 19.8 g (81% of theory).

B.p. 145° C./0.4 mbar.

(b)

5-(4-Chlorophenyl)-3-(3,4-dimethoxyphenyl)-2-methylpenta-2,4-diene-1-carboxylic acid

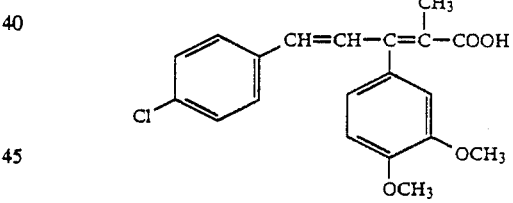

6.17 g (55 mmols) of potassium tert. butoxide were dissolved in 20 ml of absolute dimethylformamide, and a solution of 13.2 g (50 mmols) of ethyl 3-(3,4-dimethoxyphenyl)-2-methylcrotonate and 7.73 g (55 mmols) of 4-chlorobenzaldehyde in 20 ml of absolute dimethylformamide was added dropwise thereto, while stirring, and cooling on an ice bath. The resulting mixture was stirred for 6 hours at room temperature, mixed with water and acidified with hydrochloric acid. The greasy substance thus obtained was stirred with hot water, and sodium carbonate was added in small portions until a solution was formed. This aqueous solution was extracted once with toluene. The oil obtained upon acidification with hydrochloric acid was recrystallized from toluene/petroleum ether.

Yield: 11 g (61% of theory;

M.p. 164° C.

(c)
5-(4-Chlorophenyl)-3-(3,4-dimethoxyphenyl)-2-methyl-penta-2,4-diene-1-carboxylic acid morpholide

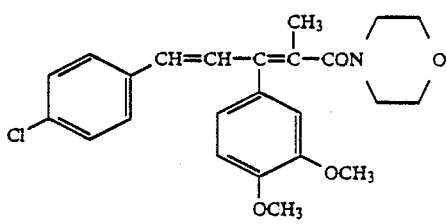

5.38 g (15 mmols) of 5-(4-chlorophenyl)-3-(3,4-dimethoxyphenyl)-2-methyl-penta-2,4-diene-1-carboxylic acid were dissolved in 30 ml of absolute tetrahydrofuran, and 3.24 g (20 mmols) of 1,1'-carbonyldiimidazole were added in portions thereto. After the evolution of $CO_2$ had ended, 1.74 (20 mmols) of morpholine were added, the mixture was allowed to stand at room temperature for 10 minutes and was then refluxed for 2 hours. The solution was evaporated in vacuo, and the residue was shaken with toluene/water. The toluene phase was again washed with water, then dried and concentrated down to about 20 ml in vacuo. This solution was purified on a chromatography column charged with 30 g of silica gel mixed with toluene. Elution was carried out first with toluene and then with a toluene-acetone mixture (90:10). The fractions containing the substance with an Rf 0.52 (toluene/acetone 70:30 on silica gel plate) were collected and evaporated in vacuo.
Yield: 4.95 g (77% of theory); oil.
Analysis: C calc. 67.36%, found 67.71%; H calc. 6.12%, found 6.10%; N calc. 3.27%, found 3.36%.

Example 41

5-(4-Chlorophenyl)-3-(3,4-dimethoxyphenyl)-penta-2,4-diene-1-carboxylic acid morpholide (a) 3,4-Dimethoxyacetophenone 215.9 g (2.75 mols) of acetyl chloride were allowed to flow into a suspension of 345.5 g (2.5 mols) of veratrole in 1400 ml of ethylene chloride. The mixture was stirred for 30 minutes at room temperature, cooled with ice-/common salt, and then 366.6 g (2.75 mols) of $AlCl_3$ were added. The mixture was stirred for 3 hours, the temperature being maintained at below 15° C. After working up and distillation using a rotary evaporator, 419.1 g (93% of theory) of an oil were obtained, b.p. 125°-127° C./0.5 mbar. A substance with a melting point of 48°-50° C. was obtained from $CCl_4$/petroleum ether.

(b) Ethyl 3,4-dimethoxy-$\beta$-methyl-cinnamate 576.2 g (2.57 mols) of triethylphosphonoacetate were added to a suspension of 291.7 g (2.6 mols) of potassium tert. butoxide, in 1.7 liters of absolute 1,2-dimethoxyethane, the mixture was stirred for 15 minutes, and then 463 g (2.57 mols) of oily 3,4-dimethoxyacetophenone were added thereto. The mixture was stirred for 7 hours at about 60° C. The solvent was removed in a rotary evaporator, the residue was mixed with water, and the aqueous mixture was extracted with ether. The ethyl 3,4-dimethoxy-$\beta$-methyl cinnamate was isolated from the ether phase with a yield of 558 g (87% of theory).
B.p. 137° C./0.17 mbar.

(c)
3-(3,4-Dimethoxyphenyl)-5-(4-chlorophenyl)-penta-2,4-diene-1-carboxylic acid A solution of 28.1 g (0.25 mol) of potassium tert. butoxide in 75 ml of dimethylformamide was prepared. At 10°-15° C., 30.7 g (0.22 mol) of 4-chlorobenzaldehyde and 50 g (0.20 mol) of ethyl 3,4-dimethoxy-$\beta$-methyl cinnamate in 125 ml of dimethylformamide were added thereto over a period of 10 minutes, while cooling. The mixture was stirred for 45 minutes without cooling, mixed with 350 ml of water and acidified with 50 ml of 6N hydrochloric acid. The product which precipitated was suction-filtered off and recrystallized from dioxane. Yield: 57.6 g (84% of theory). m.p. 226°-227° C.

(d)
3-(3,4-Dimethoxyphenyl)-5-(4-chlorophenyl)penta-2,4-diene-1-carboxylic acid morpholide 2.38 g (17.3 mmols) of phosphorus trichloride were added dropwise over a period of 10 minutes to 4.52 g (52 mmols) of morpholine in 15 ml of pyridine while cooling at $-5°$ to 0° C. After half an hour's further reaction at room temperature, 12.1 g (35 mmols) of the acid obtained in (c) suspended in 35 ml of pyridine were added all at once. The resulting mixture was allowed to stand for 3 hours at room temperature and was then stirred for half an hour at 40° C. The mixture was then combined with ice and concentrated hydrochloric acid until it reacted strongly acidic. The reaction product was precipitated by the addition of ethyl acetate, suction-filtered off, washed with water and ethyl acetate, and recrystallized from isopropanol/water. Yield: 12.3 g (85 g of theory).
M.p. 125°-126° C.

Example 42

3-(3,4-Methylenedioxyphenyl)-5-(4-chlorophenyl)-penta-2,4-diene-1-carboxylic acid isopropylamide (a)
3-(3,4-Methylenedioxyphenyl)-5-(4-chlorophenyl)-penta-2,4-diene-1-carboxylic acid 29 g (0.26 mol) of 4-chlorobenzaldehyde and 55 g (0.235 mmol) of ethyl 3,4-methylenedioxy-$\beta$-methyl cinnamate in 160 ml of dimethylformamide were added over a period of 10 minutes to a suspension of 35 g (0.25 mol) of potassium tert.butoxide in 80 ml of dimethylformamide, while cooling in such a way that the temperature did not exceed 20° C. After one hour's stirring without cooling, water and hydrochloric acid were added until the mixture reacted acidic and the product which precipitated was suction-filtered off and recrystallized from a large amount of isopropanol.
Yield: 67.8 g (87% of theory).
M.p. 205°-206° C.

(b)
3-(3,4-Methylenedioxyphenyl)-5-(4-chlorophenyl)penta-2,4-diene-1-carboxylic acid isopropylamide The phosphazo compound was prepared in the usual way from 5.9 g (0.10 mol) of isopropylamine in 25 ml of pyridine and 4.6 g (0.034 mol) of phosphorus trichloride. 22.0 g (0.067 mol) of the acid obtained in (a) were added, the mixture was stirred for 4 hours and was then allowed to stand overnight. After the addition of ice and acidification with hydrochloric acid, the mixture was extracted with ethyl acetate, and the ethyl acetate extract was washed with water and dilute sodium hydroxide and then dried and concentrated by evaporation. The residue was recrystallized from benzene/petroleum ether.

Yield: 10.8 g (43.5% of theory).
M.p. 125°–127° C.

The Rf values in the table which follows were determined on TLC plates made by the Macherey-Nagel Co. (Item No. 805 021). Eluant toluene/acetone 7:3, 22° C.

Using procedures analogous to those described in the preceding examples, the compounds of the formula

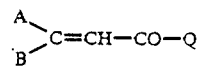

shown in the following table were also prepared:

TABLE II

| Example | Q | A | B | M.p./Rf |
|---|---|---|---|---|
| 43 | —N(CH$_3$)$_2$ | 2-OCH$_3$, 4-OCH$_3$-phenyl | —CH=CH—(4-Cl-phenyl) | Rf: 0.53 |
| 44 | —NHCH(CH$_3$)$_2$ | " | " | 146° C. |
| 45 | —N(CH$_3$)(CH$_2$—C$_6$H$_5$) | " | " | Rf: 0.71 |
| 46 | —N(C$_2$H$_5$)$_2$ | " | " | Rf: 0.63 |
| 47 | —N(CH$_3$)(n-C$_3$H$_7$) | " | " | Rf: 0.69 |
| 48 | —N(morpholino) | " | —CH=C(4-NO$_2$-phenyl) | |
| 49 | " | " | —CH=C(CH$_3$)—(3,4-di-Cl-phenyl) | |
| 50 | " | " | —CH=CH—(4-OCH$_3$-phenyl) | Rf: 0.59 |
| 51 | " | " | —CH=CH—(2-Cl-phenyl) | Rf: 0.53 |
| 52 | " | " | —CH=CH-(2-thienyl) | |
| 53 | " | " | —CH=CH—(2-OC$_2$H$_5$-phenyl) | 123° C. |
| 54 | " | " | —CH=CH—(3-Cl-phenyl) | 130° C. |

TABLE II-continued
| Example | Q | A | B | M.p./Rf |
|---|---|---|---|---|
| 55 | " | " | 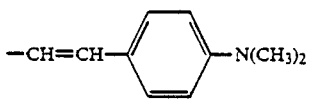 -CH=CH-C6H4-N(CH3)2 | Rf: 0.36 |
| 56 | " | " | 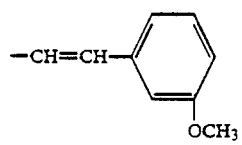 -CH=CH-C6H4-OCH3 | Rf: 0.51 |
| 57 | " | " | 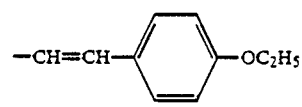 -CH=CH-C6H4-OC2H5 | Rf: 0.52 |
| 58 | " | " | 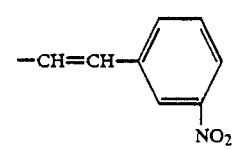 -CH=CH-C6H4-NO2 | 1522° C. |
| 59 | " | " | 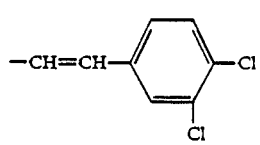 -CH=CH-C6H3-Cl2 | Rf: 0.54 |
| 60 | " | " | 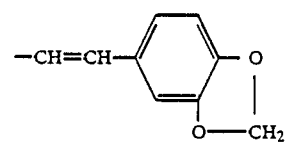 -CH=CH-(methylenedioxyphenyl) | 158° C. |
| 61 | " | 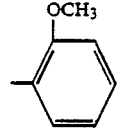 o-OCH3-phenyl | 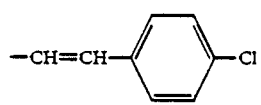 -CH=CH-C6H4-Cl | 145° C. |
| 62 | " | 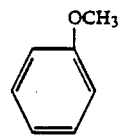 OCH3-phenyl | " | Rf: 0.62 |
| 63 | " | 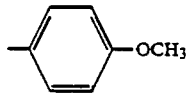 p-OCH3-phenyl | " | 122° C. |
| 64 | " | 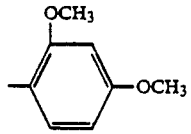 2,4-(OCH3)2-phenyl | -CH=CH-C6H5 | 149° C. |
| 65 | " |  2,3,4-(OCH3)3-phenyl | 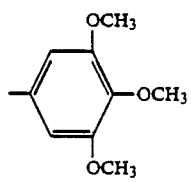 -CH=CH-C6H4-Cl | 80° C. |

TABLE II-continued

| Example | Q | A | B | M.p./Rf |
|---|---|---|---|---|
| 66 | " | 2,3-dimethoxyphenyl (OCH₃, OCH₃) | —CH=CH—C₆H₄—CH₃ (4-methyl) | |
| 67 | " | 4-chlorophenyl | —CH=CH—C₆H₄—Cl (4-chloro) | 181° C. |
| 68 | " | " | —CH=CH—C₆H₃(OCH₃)₂ (2,4-dimethoxy) | Rf: 0.51 |
| 69 | " | 3,4-methylenedioxyphenyl | —CH=CH—C₆H₄—Cl (4-chloro) | 102° C. |
| 70 | —NHCH(CH₃)₂ | " | " | 132° C. |
| 71 | morpholino (—N(CH₂CH₂)₂O) | 3,4-dimethylphenyl | —CH=CH—C₆H₄—OCH₃ | Rf: 0.62 |
| 72 | " | 4-chloro-3-nitrophenyl | —CH=CH—C₆H₅ | 151° C. |
| 73 | —NH—N(morpholino) | 3,4-dimethoxyphenyl | —CH=CH—C₆H₄—Cl | 138° C. |
| 74 | morpholino | " | —(CH=CH)₂—C₆H₅ | 80° C. |
| 75 | " | " | —CH=CH—C(CH₃)₂—(CH₂)₂—CH₃ | Rf: 0.46 |
| 76 | " | " | —CH=CH-(2-pyridyl) | Rf: 0.50 Toluene/Ethanol 8:2 |
| 77 | " | " | —CH=CH-(3-pyridyl) | 165° C. |
| 78 | " | " | —CH=CH-(4-pyridyl) | Rf: 0.13 |

TABLE II-continued

| Example | Q | A | B | M.p./Rf |
|---|---|---|---|---|
| 79 | " | " | −CH=CH−(2-furyl) | Rf: 0.46 |
| 80 | −NHCH(CH₃)₂ | " | −CH=C(CH₃)₂ | 112° C. |
| 81 | " | " | −CH=CH−CH(CH₃)₂ | 98° C. |
| 82 | " | " | −CH=C(cyclohexylidene) | 62° C. |
| 83 | −N(morpholino) | 3,4-methylenedioxyphenyl | −CH=CH−(4-Cl-C₆H₄) | 102° C. |
| 84 | " | −C₆H₅ | " | 127° C. |
| 85 | −NH−CH(CH₃)₂ | 3,4-methylenedioxyphenyl | −CH=CH−(4-Br-C₆H₄) | 126° C. |
| 86 | −N(morpholino) | 2,3-dimethoxyphenyl | −CH=C(CH₃)₂ | oil |
| 87 | " | 3,4-methylenedioxyphenyl | −CH=CH−CH(CH₃)₂ | 76° C. |
| 88 | −NH−CH(CH₃)₂ | " | −CH=C(CH₃)₂ | 133° C. |
| 89 | " | " | −C(CH₃)=C(CH₃)₂ | 97° C. |
| 90 | −N(morpholino) | 3,4-dimethoxyphenyl | −CH=C(cyclohexylidene) | oil |
| 91 | " | −C₆H₅ | −CH=CH−(2-OH-C₆H₄) | 178° C. |
| 92 | " | 2,3-dimethoxyphenyl | −CH=CH−CH(CH₃)₂ | oil |

Example 93

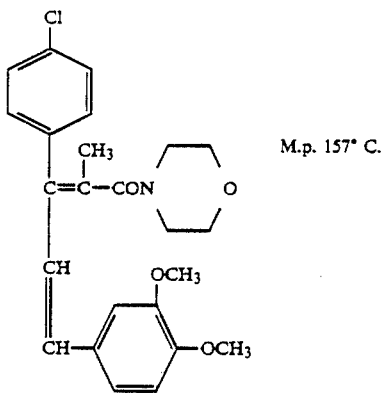

M.p. 157° C.

Example 94

2-Cyano-3-(3,4-dimethoxyphenyl)-3-phenylacrylic acid morpholide

A mixture of 12.1 g (50 mmols) of 3,4-dimethoxybenzophenone, 8.48 g (55 mmols) of cyanoacetomorpholide, 10 g of glacial acetic acid, 4 g of ammonium acetate and 100 ml of benzene was heated in a vessel equipped with a water separator, while stirring. After 5, 10 and 15 hours, respectively, 4 g of ammonium acetate and 5 g of glacial acetic acid were added each time. The mixture was heated for a total of 20 hours, and then the benzene and the glacial acetic acid were distilled off in a rotary evaporator. The residue was skaken with toluene/water, and the organic phase was again washed with water, dried and evaporated in vacuo. The residue was purified on a silica gel column, using toluene and then a toluene/acetone mixture 80:20 as eluants. The fractions containing the substance with Rf 0.56 (toluene/acetone 70:30) were evaporated completely in vacuo.

Yield: 9.7 g (51% of theory) of a viscous yellow oil. E/Z ratio 50:50.

| Analysis: | Calc.: | C-69.83%, | found: | 69.64% |
|---|---|---|---|---|
| | | H-5.86%, | | 6.07% |
| | | N-7.40%, | | 7.66%. |

Example 95

3-(3-Acetamino-4-methoxyphenyl)-3-phenylacrylic acid morpholide 3.38 g (10 mmols) of 3-(3-amino-4-methoxyphenyl)-3-phenylacrylic acid morpholide were dissolved in 20 ml of acetic anhydride, and the solution was heated for 4 hours on a boiling water bath. The solution was concentrated by evaporation in vacuo, and the residue was recrystallized from ethyl acetate/petroleum ether.

Yield: 3.1 g (81.5% of theory). M.p. 97° C.
Rf value 0.50 (toluene/acetone 30:70).

| Analysis: | Calc.: | C-69.46%, | found: | 69.67% |
|---|---|---|---|---|
| | | H-6.35%, | | 6.48% |
| | | N-7.37%, | | 7.24%. |

Example 96

3-(3-Amino-4-methoxyphenyl)-3-phenylacrylic acid morpholide 7.37 g (20 mmols) of 3-(4-methoxy-3-nitrophenyl)-3-phenylacrylic acid morpholide were dissolved in 100 ml of ethanol, then 100 ml of water were added, the mixture was heated to 50° C., and 14.7 g (70 mmols) of sodium dithionite were added while stirring. The mixture as then refluxed for one hour, the ethanol was distilled off in vacuo, and water was added. The brown greasy substance thus obtained was dissolved in toluene and purified on a silica gel column. Elution was carried out first with toluene and then with a toluene/acetone mixture 80:20. The fractions containing the substance with Rf 0.26 (toluene/acetone 70:30) were concentrated by evaporation in vacuo.

Yield: 4.4 g (65% of theory); viscous oil.
E/Z ratio 30:70.

| Analysis: | Calc.: | C-70.98%, | found: | 71.06% |
|---|---|---|---|---|
| | | H-6.55%, | | 6.68% |
| | | N-8.28%, | | 8.02% |

Example 97

3-(4-Methoxy-3-methylphenyl)-3-phenylthioacrylic acid morpholide 6.75 g (20 mmols) of 3-(4-methoxy-3-methylphenyl)-3-phenylacrylic acid morpholide and 2.22 g (10 mmols) of finely ground phosphorus pentasulfide were refluxed unit 50 ml of absolute xylene for 3 horus. After cooling, the insoluble matter was filtered off, and the filtrate was washed with water, dried and concentrated by evaporation in vacuo. This concentrate was purified on a silica gel column. Elution was carried out first with toluene and then with a toluene/diisopropylether mixture in the proportions 90:10, then in the proportions 80:20. The fractions containing the substance with Rf 0.59 (toluene/diisopropylether 1:1) were concentrated by evaporation in vacuo, and the yellow oil obtained thereby was dissolved in cyclohexane, while heating. Upon cooling, the desired substance crystallized out.

Yield: 4.0 g (56.5% of theory). M.p. 125°-127° C.

| Analysis: | Calc.: | C-71.35%, | found: | 71.52% |
|---|---|---|---|---|
| | | H-6.56%, | | 6.59% |
| | | N-3.96%, | | 4.07% |
| | | S-9.07%, | | 8.98%. |

Using the procedures analogous to those described in the preceding examples, the compounds to the formula I shown in Tables III, IV and V below were also prepared.

TABLE III

Structure: diarylidene with $R_2, R_3, R_4$ on one ring, $R_{11}, R_{12}, R_{13}$ on the other ring, connected via CH=CH to C=CH—COQ Rf values: In toluene/acetone 70:30, about 22° C.

| Example | $R_2/R_3/R_4$ | $R_{11}/R_{12}/R_{13}$ | Q | M.p. or Rf |
|---|---|---|---|---|
| 98 | 3,4-(CH$_3$O)$_2$ | 4-Cl | —N(CH$_3$)C$_4$H$_9$ | 0.70 |
| 99 | 3,4-(CH$_3$O)$_2$ | 4-Cl | —N(CH$_3$)CH(CH$_3$)—C$_2$H$_5$ | 0.61 |
| 100 | 3-NO$_2$/4-Cl | H | —N(morpholino) | 151° C. |
| 101 | 2,3,4-(CH$_3$O)$_3$ | H | —N(morpholino) | 125° C. |
| 102 | 2,3,4-(CH$_3$O)$_3$ | 4-Cl | —N(morpholino) | 127° C. |
| 103 | 3,4-(O—CH$_2$CH$_2$—O) | H | —N(morpholino) | 0.56 |
| 104 | 3,4-(O—CH$_2$CH$_2$—O) | 4-Cl | —N(morpholino) | 75–80° C. |
| 105 | 3-CH$_3$/4-CH$_3$O | H | —N(morpholino) | 137° C. |
| 106 | 3-CH$_3$/4-CH$_3$O | 4-Cl | —N(morpholino) | 151° C. |
| 107 | 3,4-(OCH$_2$O) | H | —N(morpholino) | 112° C. |
| 108 | 3-F/4-CH$_3$O | H | —N(morpholino) | 138° C. |
| 109 | 3-Cl/4-CH$_3$O | H | —N(morpholino) | 153° C. |

TABLE III-continued

| | | | | |
|---|---|---|---|---|
| 110 | 3-Br/4-CH$_3$O | H | —N(morpholino)O | 160° C. |
| 111 | 3-Br/4-CH$_3$O | 4-Cl | —N(morpholino)O | 150° C. |
| 112 | 2,5-(CH$_3$O)$_2$ | H | —N(morpholino)O | 0.58 |
| 113 | 2,5-(CH$_3$O)$_2$ | 4-Cl | —N(morpholino)O | 124° C. |
| 114 | 3-CH$_3$O/4-C$_2$H$_5$O | H | —N(morpholino)O | 0.63 |
| 115 | 3-CH$_3$O/4-C$_2$H$_5$O | 4-Cl | —N(morpholino)O | 0.60 |
| 116 | 3-CH$_3$O/4-(CH$_3$)$_2$CHO | H | —N(morpholino)O | 117° C. |
| 117 | 3-CH$_3$O/4-CH$_2$=CH—CH$_2$O | H | —N(morpholino)O | 143° C. |
| 118 | 4-C$_6$H$_5$ | 4-Cl | —N(morpholino)O | 166° C. |
| 119 | 3,5-Cl$_2$/4-NH$_2$ | H | —N(morpholino)O | 163° C. |

Analyses of the oily products in Table III

| Example | Calc. % C | Found % C | Calc. % H | Found % H | Calc. % N | Found % N |
|---|---|---|---|---|---|---|
| 98 | 69.64 | 69.67 | 6.82 | 6.73 | 3.38 | 3.17 |
| 99 | 69.64 | 69.96 | 6.82 | 6.76 | 3.38 | 3.68 |
| 103 | 73.19 | 73.41 | 6.14 | 6.26 | 3.71 | 3.41 |
| 112 | 72.80 | 73.13 | 6.64 | 6.77 | 3.69 | 3.65 |
| 114 | 73.26 | 73.33 | 6.92 | 6.95 | 3.56 | 3.57 |
| 115 | 67.36 | 67.68 | 6.12 | 6.39 | 3.27 | 2.96 |

TABLE IV

Compounds of formula

[Structure: Diphenyl-substituted acrylamide with morpholine, bearing $R_2$, $R_3$, $R_4$ on one phenyl and $R_{11}$, $R_{12}$, $R_{13}$ on the other, with C=CH—CON(morpholine)]

Rf values:
In toluene/acetone 70:30, about 22° C.

| Example | $R_2/R_3/R_4$ | $R_{11}/R_{12}R_{13}$ | M.p. or Rf | Remarks |
|---|---|---|---|---|
| 120 | 4-N(CH$_3$)$_2$ | 4-Cl | | |
| 121 | 2,4-(CH$_3$)$_2$ | " | | |
| 122 | 3,4-(CH$_3$)$_2$ | " | | |
| 123 | 3-NO$_2$/4-CH$_3$O | H | 124° C. | |
| 124 | 3,4-(CH$_3$O)$_2$ | 3,4-Cl$_2$ | | |
| 125 | 3,4-(CH$_3$O)$_2$ | H | 100° C. | Isomer mixture |
| 126 | " | H | 135–137° C. | Z Isomers |
| 127 | 3-CH$_3$/4-CH$_3$O | H | 106–110° C. | Isomer mixture |
| 128 | 3-CH$_3$/4-CH$_3$O | H | 125–127° C. | E Isomers |
| 129 | 3-CH$_3$/4-CH$_3$O | H | 115–118° C. | Z Isomers |
| 130 | 3,4-Cl$_2$ | H | 0.5 + 0.6 | |
| 131 | 3,4-(CH$_3$O)$_2$ | 3,4-(CH$_3$O)$_2$ | 70 | |
| 132 | 3,4-(CH$_3$O)$_2$ | 4-Cl | 135–137° C. | |
| 133 | 3,5-(CH$_3$)$_2$/4-CH$_3$O | H | 150° C. | |
| 134 | 3,4-(C$_2$H$_5$)$_2$ | H | 0.58 | |
| 135 | 3,4-(CH$_3$O)$_2$ | 3-Cl | Resin | |
| 136 | " | 2-Cl | 126–129° C. | |
| 137 | 3-Br/4-CH$_3$O | 4-CH$_3$O | 0.48 | Isomer mixture |
| 138 | 3-Br/4-CH$_3$O | 4-CH$_3$O | 161° C. | Z Isomers |
| 139 | 3-C$_2$H$_5$/4-CH$_3$O | H | 93° C. | |
| 140 | 3-n-C$_3$H$_7$/4-CH$_3$O | H | 0.60 | |
| 141 | 3-CH$_3$O/4-CH$_3$ | H | 0.53 | E Isomers |
| 142 | 3-CH$_3$O/4-CH$_3$ | H | 119° C. | E Isomers |
| 143 | 3-Cl/4-CH$_3$O | 3-Cl, 4-CH$_3$O | 0.50 | |
| 144 | 3-CH$_3$/4-OH | H | 0.42 | |
| 145 | 3-NH$_2$/4-CH$_3$O | 4-Cl | | |
| 146 | 3,4-(CH$_3$O)$_2$ | 2-F | 118–127° C. | |
| 147 | 2,3-(CH$_3$)$_2$/4-CH$_3$O | H | 171–174° C. | |
| 148 | 3-CH(CH$_3$)$_2$/4-CH$_3$O | H | 134–136° C. | |
| 149 | 3-CH$_3$/4-NO$_2$ | 4-CH$_3$O | 0.42 | |
| 150 | 3-NH$_2$/4-Cl | H | 65–67° C. | |
| 151 | 3-CH$_3$/4-CH$_3$O | 3-CH$_3$/4-CH$_3$O | 0.47 | |
| 152 | 3-NHCOCH$_3$/4-CH$_3$O | 4-Cl | | |

Analyses of the oily products in Table IV

| Example | Calc. % C | Found % C | Calc. % H | Found % H | Calc. % N | Found % N |
|---|---|---|---|---|---|---|
| 122 | 70.47 | 70.71 | 6.23 | 6.10 | 3.94 | 4.05 |
| 124 | 59.72 | 59.87 | 5.01 | 5.21 | 3.32 | 3.17 |
| 130 | 62.99 | 63.20 | 4.73 | 4.67 | 3.87 | 3.70 |
| 134 | 79.05 | 78.96 | 7.79 | 7.78 | 4.01 | 3.86 |
| 135 | 65.03 | 64.74 | 5.68 | 5.77 | 3.61 | 3.60 |
| 137 | 58.34 | 58.67 | 5.13 | 5.25 | 3.24 | 3.22 |
| 140 | 75.59 | 75.89 | 7.45 | 7.69 | 3.83 | 3.69 |
| 141 | 74.75 | 74.55 | 6.87 | 7.01 | 4.15 | 4.17 |
| 143 | 59.72 | 59.91 | 4.98 | 5.12 | 3.32 | 3.18 |
| 144 | 74.30 | 74.61 | 6.50 | 6.73 | 4.33 | 4.01 |
| 145 | 70.98 | 71.06 | 6.55 | 6.68 | 8.28 | 8.16 |
| 148 | 75.62 | 75.61 | 7.40 | 7.35 | 3.84 | 4.03 |
| 149 | 65.97 | 65.73 | 5.76 | 5.91 | 7.33 | 7.19 |
| 151 | 72.42 | 72.54 | 7.13 | 7.26 | 3.67 | 3.50 |

TABLE V

[Structure: Phenyl-substituted with $R_2$, $R_3$, $R_4$ connected via C=CR$_1$—CON(morpholine), with B substituent]

| Example | $R_1$ | $R_2/R_3/R_4$ | B | M.p. or Rf |
|---|---|---|---|---|
| 153 | H | 3,4-(CH$_3$O)$_2$ | —C(CH$_3$)=CH—C$_6$H$_4$-4-Cl | 127° C. |
| 154 | H | " | —C(CH$_3$)=CH—C$_6$H$_5$ | 145° C. |
| 155 | Br | 3-Br/4-CH$_3$O | 2-Br-4-OCH$_3$-phenyl | 93° C. |
| 156 | H | 3,4-(CH$_3$O)$_2$ | 2-Naphthyl | Resin Analysis |
| 157 | H | " | 1-Naphthyl | 0.43 |
| 158 | H | " | cyclohexyl (—H) | 117–120° C. |
| 159 | H | " | —CH$_2$C$_6$H$_5$ | 0.46 + 0.56 |
| 160 | H | " | —CH(CH$_3$)$_2$ | |
| 161 | H | H | 4-OCH$_3$-naphthyl | 228–231° C. |
| 162 | H | 3,4-(CH$_3$O)$_2$ | 2-thienyl | 130–132° C. |
| 163 | —CH$_3$ | " | —C$_6$H$_5$ | 0.50 + 0.60 |
| 164 | —CN | " | —C$_6$H$_5$ | |

Analyses relating to Table V

| Example | Calc. % C | Found % C | Calc. % H | Found % H | Calc. % N | Found % N |
|---|---|---|---|---|---|---|
| 156 | 74.44 | 74.69 | 6.20 | 6.48 | 3.47 | 3.29 |
| 157 | 74.44 | 74.73 | 6.20 | 6.40 | 3.47 | 3.32 |

TABLE V-continued

[Structure: benzene ring with R2, R3, R4 substituents and C=CR1—CON-morpholine group, with B]

| | | | | | | |
|---|---|---|---|---|---|---|
| 159 | 71.93 | 72.05 | 6.81 | 6.92 | 3.81 | 3.77 |
| 160 | 67.71 | 67.48 | 7.84 | 7.79 | 4.39 | 4.33 |
| 163 | 71.91 | 72.20 | 6.86 | 6.98 | 3.81 | 3.74 |

The compounds of the present invention, that is, those embraced by formula I and acid addition salts, thereof, have useful properties. More particularly, they are highly effective biocidal agents against phytopathogenic fungi, particularly genuine mildew, false mildew (such as Plasmopara and Phytophthora), scurf, grey mould and rust fungi. Since they have very low phytotoxicity, the new compounds may be used in virtually all crops of useful and ornamental plants, for example cereals such as corn, wheat, rye, oats and rice, in tomatoes, cucumbers, beans, potatoes, beets and in viticulture and fruit growing and on roses, carnations and chrysanthemums.

The new compounds act on leaves and also have a systemic effect. Thus, with several of the compounds according to the invention, used in a leaf treatment against Plasmopara in a concentration of active substance of between 20 and 100 ppm, the fungi are completely killed off (e.g. with the compounds according to Examples 1, 5, 11, 13, 21, 23, 37, 38, 43, 78, 90, 104, 105, 109, 121, 125, 127). For combatting Phytophthora, concentrations of active substance of 100 ppm or sometimes less are generally sufficient for a satisfactory effect (e.g. with the compounds according to Examples 6, 21, 24, 35, 37, 39, 40, 50, 65, 88, 101, 105, 106, 114, 125, 127, 130, 149, 157, 162). It is advantageous in many cases to combine the compounds according to the invention with known fungicidally active substances. The effect of the combinations is in some cases clearly greater than a purely additive effect.

Combination partners

Manganese ethylene-bis-dithiocarbamate (Maneb)
Manganese-zinc ethylene-bis-dithiocarbamate (Mancozeb)
Zinc ethylene-bis-dithiocarbamate (Zineb)
N-trichloromethylthio-tetrahydrophthalimide (Captan)
N-trichloromethylthiophthalimide (Folpet)
N-(1,1,2,2-tetrachloroethylthio)tetrahydrophthalimide (Captafol)
2,3-dicyano-1,4-dithiaanthraquinone (Dithianon)
Zinc-(N,N'-propylene-bis-dithiocarbamate) (Propineb)
Copper oxychloride
Sodium-4-dimethylaminobenzenediazosulfonate (Fenaminosulf)
Triphenyl-tin acetate (Fentinacetate)
Triphenyl-tin hydroxide (Fentinhydroxyd)
Iron dimethyldithiocarbamate (Ferbam)
N-(2-Furoyl)-N-(2,6-xylyl)-DL-alanine (Furalaxyl)
3-(Dimethylamino)propylcarbamate (Propamocarb)
N-Ethyl-N-(3-dimethylamino)thiocarbamate (Prothiocarb)
Tetramethylthiuramdisulfide (Thiram)
N-Dichlorofluoromethylthio-N,N'-dimethyl-N-p-tolyl-sulfamide (Tolylfluamid)
N-(2-Methoxyacetyl)-N-(2,6-xylyl)alanine (Metalaxyl)
Zinc dimethylthiocarbamate (Ziram)
N-Dichlorofluoromethylthio-N',N'-dimethyl-N-phenyl-sulfamide (Dichlofluanid)
3-Trichloromethyl-5-ethoxy-1,2,4-thiadiazole (Etridazol)
Tri[amino-zinc-ethylene-bis-(dithiocarbamate)]tetrahydro-1,2,4,7-dithiadiazocine-3,8-dithione polymer (Metiram)
Aluminum tris(o-ethylphosphate) (Phosethyl)
2-Cyano-N-(ethylcarbamoyl)-2-methyloximino-acetamide (Cymoxanil)
N-(3-Chlorophenyl)-N-(tetrahydrofuran-2-on-3-yl)-cyclopropanecarbonamide (Cyprofuran)
Tetrachloro-isophthalodinitrile (Chlorothalonil)
6-Methyl-2-oxo-1,3-dithio[4,5-b]-quinoxaline (Chinomethionate)
4-Cyclododecyl-2,6-dimethylmorpholine (Dodemorph)
1-Dodecylguanidiniumacetate (Dodin)
Diisopropyl-5-nitroisophthalate (Nitrothal-isopropyl)
2,4-Dichloro-α-(pyrimidin-5-yl)benzhydryl alcohol (Fenarimol)
1-(β-Allyloxy-2,4-dichlorophenethyl)imidazole (Imazalil)
3-(3,5-Dichlorophenyl)-N-isopropyl-2,4-dioxoimidazolidine-1-carboxamide (Iprodion)
Sulfur
2,3-Dihydro-6-methyl-5-phenylcarbamoyl-1,4-oxythiine-4,4-dioxide (Oxycarboxin)
N-(3,5-Dichlorophenyl)-1,2-dimethylcyclopropane-1,2-dicarboximide (Procymidon)
6-Ethoxycarbonyl-5-methylpyrazolo[1,5]pyrimidin-2-yl-0,0-dimethylphosphorusthioate (Pyrazophos)
2-(Thiazol-4-yl)-benzimidazole (Thiabendazol)
1-(4-Chlorophenoxy)-3,3-dimethyl-1-(1,2,4-triazol-1-yl)-2-butanone (Triadimefon)
1-(4-Chlorophenoxy)-3,3-dimethyl-1-(1,2,4-triazol-1-yl)-butanol (Triadimenol)
3-(3,5-Dichlorophenyl)-5-methyl-5-vinyloxyzolidine-2,4-dione (Vinclozolin)
Methylbenzimidazol-2-ylcarbamate (Carbendazin)
2,4,5-Trimethyl-N-phenyl-3-furancarboxamide (Methfuroxam)
β-[1,1'-Biphenyl]-4-yl-oxy)-α-(1,1-dimethylethyl-1H-1,2,4-triazol-1-ethanol (Bitertanol)
2-(2-Furyl)benzimidazole (Fuberidazol)
5-Butyl-2-ethylamino-6-methylpyrimidin-4-ol (Ethirimol)
2-Methyl-3-furanilide (Fenfuram)
Bis-(8-guanidino-octyl)amine (Guazatin)
N-Cyclohexyl-N-methoxy-2,5-dimethylfuran-3-carboxylic acid amide (Furmecyclox)
2-Chloro-4'-fluoro-α-(pyrimidin-5-yl)benzhydryl alcohol (Nuarimol)
Methyl-1-(butylcarbamoyl)benzimidazolcarbamate (Benomyl)
0,0-Diethylphthalimidophosphonothioate (Dithalin)
7-Bromo-5-chloroquinolin-8-yl-acrylate (Halacrimat)
1-[2-(2,4-Dichlorophenyl)-4-propyl-1,3-dioxolan-2-ylmethyl]-1H-1,2,4-triazole (Propiconazol)
Dimethyl-4,4'-(o-phenylene)bis(thioallophanate) (Thiophanat-methyl)
1,4-Bis(2,2,2-trichloro-1-formamidoethyl)piperazine (Triforine)
2,6-Dimethyl-4-tridecylmorpholine (Tridemorph)
4-{3-[4-(1,1-Dimethyl-ethyl)phenyl]-2-methyl}-propyl-2,6-(cis)dimethylmorpholine (Fenpropemorph)

1-[2-(2,4-Dichlorophenyl)-4-ethyl-1,3-dioxolan-2-ylmethyl]-1H-1,2,4-triazole (Etaconazol)
1-[1-(2,4-Chlorophenyl)-4,4-dimethyl-3-hydroxy-2-pentyl]-1,2,4-triazole (Diclobutrazol)
2,4-Dichloro-6-(2-chloroanilino)-1,3,5-triazine (Anilazin)
(2-Iodo-N-phenylbenzamide (Benodanil)
2-sec.butyl-4,6-dinitrophenyl-3-methylcrotonate (Binapacryl)
5-Butyl-2-(ethylamino)-6-methyl-4-pyrimidinyl dimethylsulfonate (Buprimat)
2,4-Dinitro-6-oxtylphenylcrotinate (Dinocap)
5,6-Dihydro-2-methyl-1,4-oxathiine-3-carbanilide (Carboxin) N-Propyl-N-[(2,4,6-trichlorophenoxy)-2-ethyl]-imidazole-1-carbonamide (Prochloraz).

For use in plant protection, the new compounds are processed in the usual way with excipients and/or carriers to produce conventional forms of pesticidal agents, e.g. solutions, emulsions or solution concentrates, wettable powders and dusting powders. If they are to be used in conjunction with other active substances, they may be made into combined formulations or, for example, tank mixtures. If necessary, the concentrates are diluted with water before use to produce spray liquors containing between about 0.001 and 1% by weight of active substance. For use as low volume or ultra-low volume formulations, the content of active substance may also be considerably higher (up to about 20 or 90% by weight, respectively).

The following examples illustrate fungicidal compositions comprising a compound of the present invention as an active ingredient and represent the best modes contemplated of using the invention.

Example 164

Wettable powder
 20 parts by weight of a compound of the formula I
 20 parts by weight of kaolin
 5 parts by weight of sodium sulfate
 2 parts by weight of prepared chalk
 9 parts by weight of calcium ligninsulfonate
 1 part by weight of diisobutylnaphthalene sodium sulfonate
 43 parts by weight of siliceous chalk The ingredients are ground. For use, the composition is suspended in a quantity of water such that the concentration of active substance is about 0.001 to 0.5% by weight.

Example 165

Emulsion concentrate
 15 parts by weight of a compound of the formula I
 10 parts by weight of the triethylamine salt of dodecylbenzenesulfonic acid
 75 parts by weight of dimethylformamide While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

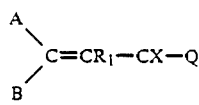

wherein
A is

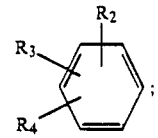

B is $Y-(CR_5=CR_6)_k-$;
Q is

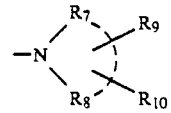

X is O or S;
Y is

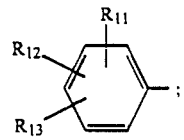

k is 1;
$R_1$ is hydrogen, $C_{1-4}$ alkyl or cyano;
$R_2$ and $R_{11}$ are each hydrogen, halogen, nitro, $C_{1-4}$ alkyl, alkoxy optionally mono- or polysubstituted by fluorine or chlorine, $C_{3-4}$ alkynyloxy, amino, $-NH(C_{1-4}alkyl)$, $-N(C_{1-4}alkyl)_2$, cyano, phenyl, $C_{3-6}$ cycloalkyl, $C_{3-4}$ alkenyloxy, hydroxy($C_{1-4}$alkyl), $-NH-COR_6$, $-CO_2R_6$, $CONR_7R_8$, $C_{2-8}$ alkyl interrupted by oxygen, or

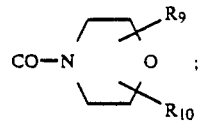

$R_3$, $R_4$, $R_{12}$ and $R_{13}$ are each hydrogen, halogen, $C_{1-4}$ alkyl, $C_{1-4}$ alkoxy, $(C_{1-4}$ alkyl)-$S(O)_p$ (p=0, 1 or 2), hydroxy or $(C_{1-4}$ alkanoyl)oxy; or
$R_3/R_4$ and $R_{12}/R_{13}$ together are methylene dioxy or ethylenedioxy attached to two adjacent carbon atoms of the phenyl ring;
$R_5$ and $R_6$ are each hydrogen or $C_{1-4}$ alkyl;
$R_7$ and $R_8$ together are a $C_{3-5}$ alkylene chain which may be interrupted by $-O-$, $-NR_6-$ or $-S(O)_q-$ (where q=0, 1 or 2); and
$R_9$ and $R_{10}$ are each hydrogen or $C_{1-4}$ alkyl;
or a non-toxic, pharmacologically acceptable acid addition salt thereof.

2. A compound of claim 1, where X is oxygen.
3. A compound of claim 1, where Q is

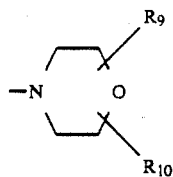

and $R_9$ and $R_{10}$ are the meanings defined in claim 1.

4. A compound of claim 1, where A is 3,4-disubstituted phenyl.

5. A compound of claim 1, where $R_1$ is hydrogen.

6. A compound of claim 3, where $R_9$ and $R_{10}$ are hydrogen.

7. A biocidal composition consisting essentially of an inert carrier and an effective biocidal amount of a compound of claim 1.

8. The method of killing phytopathogenic fungi which comprises contacting said fungi with an effective fungicidal amount of a compound of claim 1.

* * * * *